United States Patent [19]
LeBlanc

[11] Patent Number: 4,640,563
[45] Date of Patent: Feb. 3, 1987

[54] UNIVERSAL CLASP STRUCTURE FOR EXTERNAL ELECTRODE PROBES

[75] Inventor: James R. LeBlanc, Augusta, Ga.

[73] Assignee: The LeBlanc Corporation, Augusta, Ga.

[21] Appl. No.: 743,147

[22] Filed: Jun. 10, 1985

[51] Int. Cl.⁴ ............................................ H01R 11/00
[52] U.S. Cl. .................................. 339/32 M; 128/639; 339/29 B
[58] Field of Search .................. 128/639–641, 128/802, 793, 798, 643, 644; 339/32 R, 32 M, 29 B, 124, 261

[56]   References Cited
U.S. PATENT DOCUMENTS 3,868,165  2/1975  Gonser ................................. 339/261
3,914,007 10/1975  Seidler ................................. 339/261
4,449,772  5/1984  Johnson, III ....................... 339/29 B
4,453,791  6/1984  Ledbetter ........................... 339/29 B Primary Examiner—Gil Weidenfeld
Assistant Examiner—Paula A. Austin
Attorney, Agent, or Firm—Raymond N. Baker

[57]   ABSTRACT

Improved clasp structure for use with both planar-type and curvilinear button-type external electrode sensors for electrical transfer of ECG signals. An integral connector on this universal-type clasp structure provides mechanically interlocked connection with a shielded cable to significantly reduce signal interference from external electrical sources. This new clasp structure can be used and reused in a sterile environment; it can be sterilized in a steam autoclave and is partially covered with sterilized surgical tubing so as to prevent pick-up of stray patient signals.

10 Claims, 10 Drawing Figures

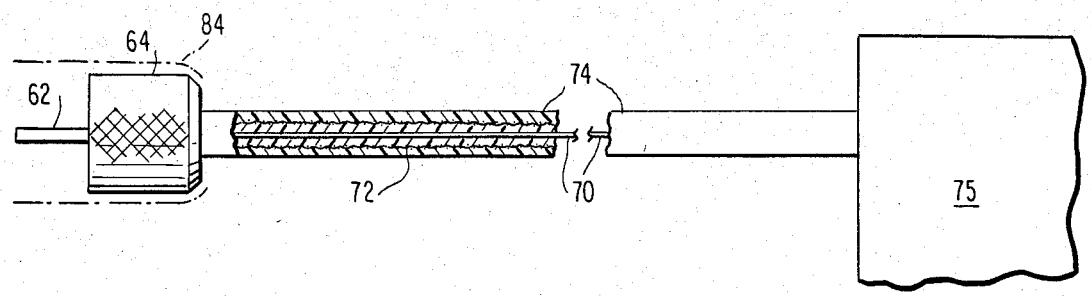
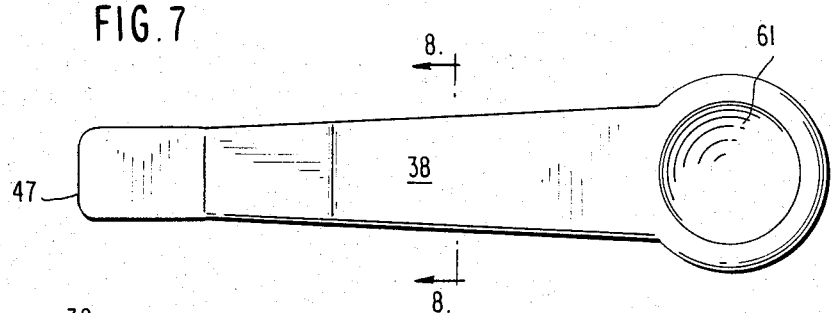
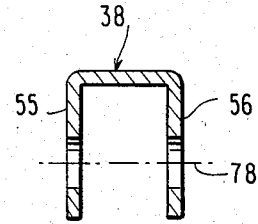
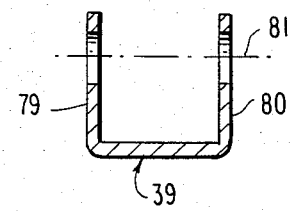
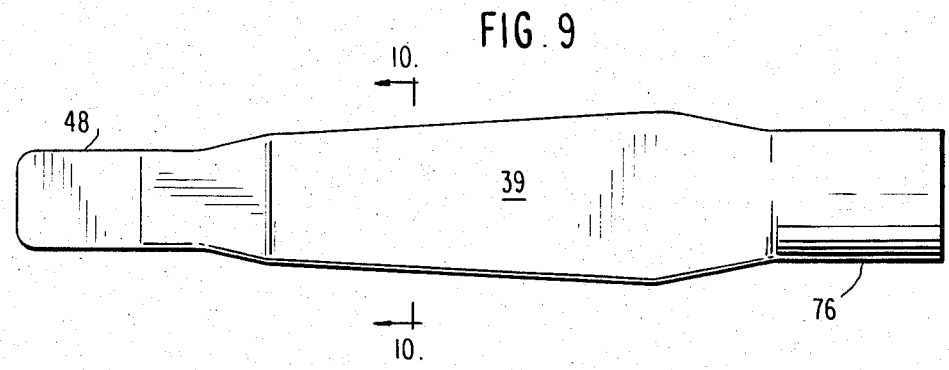

UNIVERSAL CLASP STRUCTURE FOR EXTERNAL ELECTRODE PROBES

This invention relates to improved electrical clasp structures for transferring electro-medical signals. In its more specific aspects, this invention is concerned with a universal clasp structure capable of being used with differing types of external electrode sensors for substantially interference-free transfer of body or skin signals to electrical equipment for making ECG measurements or displays.

External electrode sensors for ECG readings are placed in contact with a patient at selected locations about the torso and limbs. These sensors are held adhesively to the skin surface and include a conductive gel to increase responsiveness to body or skin signals. Two types of external electrode sensors are in general use with the selection of either type being dependent on measuring conditions. One type, used when a patient is in a prone position for short-term measurements, comprises a thin sheet form of electrode with an exposed planar tab for transferring sensed electrical signals. Another type, generally used for longer-term measurements, for example when the patient is exercising, provides a curvilinear configuration contact, such as a male "snap-on" button (similar to the type of button used as a clothing fastener), for transferring such signals. In the past, differing types of connectors had to be made available for use with such differing types of sensors.

An alligator clip with jagged-edge gripping means has typically been used on the exposed planar contact tab. However, such an alligator clasp has certain disadvantages and, in particular, cannot provide desired electrical contact and stability with a curvilinear surface contact. Therefore, a female connector of some type, which would e.g. snap over a male probe button, was required when taking signals from an exercising patient. Because of the differing types of sensors and connectors, delays were encountered in making selections and setting up for measurements for different purposes.

Also, as part of each prior type of structure, a lead wire was soldered to the connector. This lead wire, which generally had a length of about six inches, was provided with electrical insulation to avoid picking up stray signals from its contact with the patient. However, electrical interference from external sources picked up by such lead wire would cause readings to be non-intelligible or spurious. For example, fluorescent lights in the area where readings were being taken generally had to be turned off, with resultant inconvenience, to help avoid such electrical interference. These and other disadvantages of the prior art have impeded ECG measurement technology.

The present invention surmounts these problems and disadvantages by providing a single universal type of electrical clasp structure for obtaining accurate ECG measurements from the different types of external electrode structures used for sensing patient signals.

Other advantages and contributions of the invention, along with details of the present invention and comparisons to prior art structures, are described in relation to the accompanying drawings, in which:

FIG. 6 is a side view, partially in cross section, showing the thumb nut connector of the present invention used with a shielded cable leading to measuring equipment, with the latter shown schematically;

FIG. 7 is a top plan view of one clip arm of the clasp structure of FIG. 1;

FIG. 8 is a cross-sectional view of the clip arm of FIG. 7 taken along the lines 8—8;

FIG. 9 is a bottom plan view of the remaining clip arm of the clasp structure of FIG. 1; and FIG. 10 is a cross-sectional view of the clip arm of FIG. 9 taken along the lines 10—10.

FIGS. 1 and 2 are presentations of the differing external electrode patient sensor structures which have been and are in general use.

Figure 1:
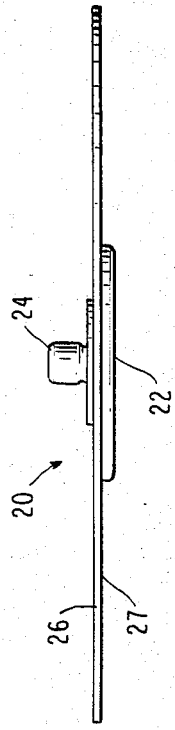
FIG. 1 is a schematic cross-sectional view of the planar tab type of external electrode which has been in general use.

In the planar tab type of sensor of FIG. 1, an elongated sheet electrode 12 is utilized; while shown schematically as metallic, this electrode generally takes the form of a thin sheet of plastic with a plated electrode of silver-silver chloride which is electrically conductive. The conductive planar electrode is subdivided by insulating structure into a signal-sensing portion 14 and a signal transfer portion, tab 15. A thin piece of foam rubber, with adhesive bottom surface 17, covers the outer surface of the patient signal sensing portion 14 and circumscribes portion 14 for holding the assembly to the patient's skin. A thin piece of electrically-insulating plastic tape 20 is also joined to a portion of the adhesive surface 17 so as to prevent contact of the electrically-conductive tab 15 with the patient's skin. Contact tab 15 is thus accessible for transfer of electrical signals sensed by portion 14 which is in contact with a patient.

Figure 2:
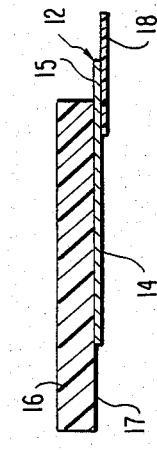
FIG. 2 is a schematic cross-sectional view of a curvilinear configuration type of sensor contact, in the form of a male "snap-on" button, which has been in general use.

FIG. 2 shows curvilinear configuration contact sensor structure 20 which includes a bottom surface 22 which is responsive to body or skin signals and, thereabove, a male contact button 24. The sensor structure is held within a circular pad 26 which has an adhesive covered bottom surface 27.

Figure 3:
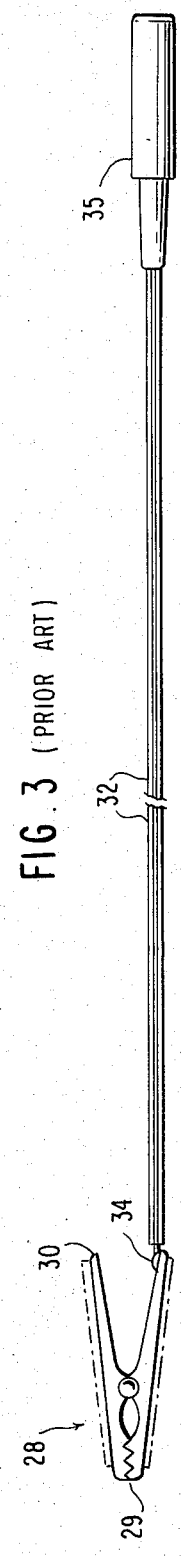
FIG. 3 is a schematic view, partially in cross section, of prior art connector structure which has been used for transfer of electro-medical signals.

"Alligator" gripping means have conventionally been used with the planar tab-type sensor of FIG. 1. As shown in FIG. 3, an alligator clip 28 includes jagged edge jaws 29 at its working end and handle means 30, for opening such jaws, at its opposite end. As a part of the prior art connector structure, a lead wire 32 was electrically connected by solder 34 to one arm of the alligator clip 28. At the opposite longitudinal end of such lead wire 32, a female receptacle 35 was provided for receiving a male member (not shown) for electrical connection to measuring equipment. Lead wire 32 of the type shown was electrically insulated to avoid picking up signals by direct contact with a patient's body but was not otherwise shielded. Such lead wire was also used with the curvilinear-configuration contact structure of FIG. 2, e.g. see U.S. Pat. No. 3,740,703 of June 19, 1973.

Because of the lead wire and other aspects of prior connector structures, such structures could not be sterilized for repeated use in sterile environments, had short-term life expectancy in non-sterile environments and, in general, did not provide for optimum recovery of the low-energy-level patient signals available.

The present invention avoids the problems associated with selections of different connector structures, and other difficulties of the prior art, by providing a universal clasp structure capable of being used with the differing types of external electrode sensors used for electromedical measurements, and by eliminating the need for an extension lead wire as used in the prior art.

Figure 4:
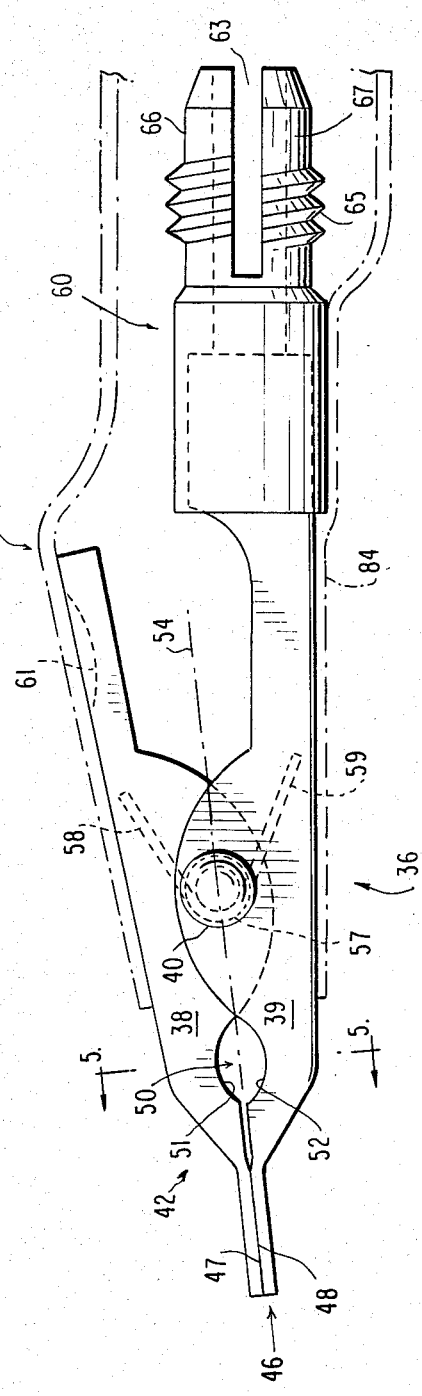
FIG. 4 is a side view, partially in cross section, of an embodiment of the universal clasp structure of the present invention.

Universal clasp structure 36 of FIG. 4 includes a pair of elongated clip arms 38, 39 pivotally articulated in relation to each other about mechanical interconnecting means in the form of rivet 40. Electrical contact means are located at the longitudinal working end 42 of the clip arms and handle means are located at the remaining opposite longitudinal end 44 of the clip arms; interconnecting rivet 40 is located longitudinally intermediate such working end and handle end of the clip arms.

Elongated nose 46 which provides planar connector means at working end 42 includes planar contact surface 47 on clip arm 38 and planar contact surface 48 on clip arm 39. Curvilinear configuration connector means 50, which is located between nose 46 and rivet 40, is defined by curved surface 51 on arm 38 and curved surface 52 on arm 39. Surfaces 51, 52 are curvilinear as shown in elevation in FIG. 4 to provide optimum electrical contact with the curvilinear periphery of the male button type of external electrode sensor.

Figure 5:
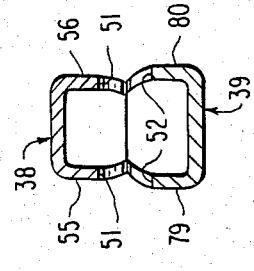
FIG. 5 is a cross-sectional view taken along the lines 5—5 of FIG. 4.

A cross-sectional view, in a plane perpendicular to longitudinal axis 54 through such curvilinear-configuration connector means 50, is shown in FIG. 5; lateral spacing between dependent legs, such as 55, 56 of clip arm 38, can be selected.

The planar (46) and curvilinear-configuration (50) connector means at the working end of clasp 36 are biased in confronting relationship by torsion spring 57 wound around the shaft of rivet 40; such spring includes torsion arm 58 in contact with the inner surface of clip arm 38 and torsion arm 59 in contact with the inner surface of clip arm 39.

The planar surfaces 47, 48 at the distal working end of clasp structure 36 make full surface contact with a planar tab, such as tab 15 shown in FIG. 1.

The invention departs further from prior art structures by establishing integral connector 60 at the handle end of the clasp 36; in addition to other advantages, this eliminates the electrical lead extension required by the prior art and significantly reduces the opportunity for signal interference from external electrical sources.

At least one of the elongated clip arms includes an integral connector means at its handle end. For example, as shown in FIG. 4, chuck-type connector 60 is an integral part of clip arm 39. In the illustrated embodiment, clip arm 38 includes finger indentation surface 61 to facilitate moving the clip arms in relation to each other about rivet 40.

In completing connection to measuring equipment with the illustrated embodiment, a male probe 62 (shown in FIG. 6) is inserted into central opening 63 (FIG. 4) of integral connector means 60 and thumb nut 64 (FIG. 6) is threaded onto external threads 65 on collet 66 to provide a mechanically secure electrical contact. Collet 66 is divided axially into four quadrants, such as 67, by longitudinally extending slots which cross at the central opening 63; dividing collet 66 into four quadrants facilitates mechanical interlocking as thumb nut 64 is threaded onto collet 66 to move the quadrants radially inwardly about male member 62.

As shown in FIG. 6, male member 62 is integral with electrical cable 70 which is shielded from electrical interference. Electrical shield 72 is electrically insulated from cable 70, is covered by outer electrical insulation 74, and is electically grounded in a manner known in the coaxial cable art. Such shielded cable extends to appropriate measuring equipment 75, shown schematically.

While a female receptacle 63, as shown on clip arm 39, for receiving male member 62 is preferred for standardization purposes, a male member and thumb nut on clip arm 39 could be joined to a female receptacle on the shielded cable structure without departing from the integral mechanically-interlocked connector concept of the present invention.

In fabricating the illustrated clasp 30, clip arm 39 is formed with cylindrical configuration end 76 (FIG. 9); the cylindrical opening in connector means 60 is placed over end 76 and welded to clip arm 39.

The extent of surface area provided at nose 46 for contact with a planar tab (of the FIG. 1 type) is shown by the top plan view of FIG. 7 and the bottom plan view of FIG. 9.

In the cross-sectional view of the clip arm 38 of FIG. 8, the apertures through lateral side legs 55, 56 of the "U" shaped configuration provide for reception of the shaft of rivet 40 along axis 78. Similarly, in the cross-sectional view of FIG. 10, the apertures in lateral side legs 78, 79 of clip arm 39 provide for reception of the rivet shaft along axis 81; when clip arms 38, 39 are in articulated assembly, axis 78 of FIG. 8 and axis 81 of FIG. 10 are coincident; such rivet shaft contact on both lateral sides of arms 38, 39 provides lateral stability for clasp 36.

As shown in dotted lines in FIG. 4, the outer metal framework of clasp 36 is covered in part by electrical insulation sleeve 84. Such outer surfaces of the clip arms are electrically insulated to prevent pick-up of stray signals from a patient's body by contact with the patient adjacent to the sensor contact. Resilient surgical tubing is preferred for such electrical insulation of the clasp. Such tubing fits over the clasp structure and extends longitudinally from contiguous to the curvilinear-configuration means 50 to cover the clasp handle end 44, including the outer cylindrical surface of integral connector means 60 and thumb nut 64 (FIGS. 4 and 6).

The invention is adaptable to use and reuse in a sterile environment. After use, the surgical tubing can be removed and the clasp and surgical tubing are sterilized in a steam autoclave; the sterilized surgical tubing is placed over the sterilized clasp for reuse. The capability of sterilizing the entire clasp structure in a steam autoclave is an advantage which was not available with prior art structures (e.g. as shown in FIG. 3) because of the lead wire construction.

In practice, the clip arms can be fabricated from low carbon flat-rolled steel (nominal thickness about 0.020") with the entire structure coated by medical-grade plating practice with nickel so that no portion of the clasp is subject to rusting. Rivet 40 and torsion spring 57 are preferably stainless steel.

Materials and approximate dimensions for a typical embodiment are as follows:

| Length: | |
|---|---|
| clip arm 38 | 1.2" |

| -continued | |
|---|---|
| clip arm 39 and cylindrical sleeve of integral connector 60 | 1.5" |
| planar clamp surface 47, 48 | .2" |
| between surfaces 47, 48 and curvilinear opening 50 | .1" |
| curvilinear opening 50 | .14" |
| between curvilinear opening 50 and centerline of rivet 40 | .2" |
| between centerline of rivet 40 and start of cylindrical sleeve portion of integral connector 60 | .65" |
| cylindrical sleeve of integral connector 60 | .25" |
| Width: | |
| planar clamp surfaces 47, 48 | .15" |
| between lateral sides of clip arms at curvilinear opening 50 | .180" |
| Height: | |
| combined legs 55 and 79 at centerline of curvilinear opening 50 | .245" |
| combined legs 55 and 79 measured from centerline of rivet 40 | .3" |
| aperture opening each leg | .08" |
| Diameter: | |
| cylindrical sleeve 76 end of clip arm 39 | .2" |
| central opening 63 | .05" |
| collet 66 | .2" |
| thumb nut | .4" |
| Clasp Insulation: | |
| modified surgical tubing, steam sterilizable | |
| length | 1 5/16" ± 1/16" |
| inner diameter | ⅜" |
| wall thickness | 1/32" |
| interior finish | satin |

While configurational aspects have been shown and dimensional data and material characteristics set forth for purposes of describing the invention to enable those skilled in the art to make and use the same, it is understood that modifications can be made in these specifics in the light of the above teachings; therefore, for purposes of determining the scope of the present invention, reference shall be had to the appended claims.

I claim:

1. Universal clasp structure capable of being releasably secured to either a planar tab-type or curvilinear-surface button-type contact of an EKG external electrode sensor for electrical transfer of body or skin signals enabling accurate measurements to be made with minimal electrical interference, comprising:

a pair of elongated electrically-conductive clip arms, each clip arm having electrical contact means contiguous to one of its longitudinal ends and means capable of functioning as a handle at its remaining longitudinal end, mechanical means pivotally interconnecting said pair of clip arms intermediate their longitudinal ends in articulated relationship, with said electrical contact means at said one longitudinal end of each clip arm confronting each other and said handle means at the remaining longitudinal end of said clip arms being disposed for articulated movement toward each other about said mechanical interconnecting means to open said confronting contact means, spring means acting on said clip arms as pivotally interconnected to bias said confronting electrical contact means of said clip arms together, said electrical contact means on each said clip arm including:

a planar surface contact, and a curvilinear configuration contact, said planar surface contact extending from the distal end of each said clip arm toward said mechanical interconnecting pivot means for said arms presenting an elongated nose portion of substantially flat configuration in longitudinal cross section, said curvilinear contact of each clip arm being located intermediate said planar surface contact and said interconnecting means, and electrical coupling means located at said handle end of at least one of said clip arms for electrically connecting said clasp structure directly to a shielded electrically conductive cable for transferring sensed electrical signals to electrical measurement equipment.

2. The structure of claim 1 further including:

an electrical insulation covering external peripheral surfaces of said electrically conductive clip arms between said curvilinear-configuration contact means and said handle means longitudinal end of each clip arm to electrically insulate said clip arms from body or skin signals other than through said contact means at said one longitudinal end of each said clip arm.

3. The structure of claim 1 in which said planar contact surface of each clip arm has a width dimension of about 0.15" and a length dimension of about 0.2", and each said lateral leg of each said clip arm presents a curvilinear-configuration contact.

4. The structure of claim 1 in which the electrical coupling means located at such handle end of at least one of said clip arms forms part of a chuck assembly.

5. The structure of claim 4 in which said coupling means comprises:

an elongated cavity means, and an elongated male member, said cavity means being oriented for receiving such male member.

6. The structure of claim 5 in which said elongated cavity means is defined by:

externally threaded collet means integral with said clasp, said male member is electrically joined to said shielded electrically conductive cable, and an internally threaded nut means is provided for mechanically interlocking said male member in electrical contact with said clip arm within said cavity means.

7. The structure of claim 6 further including:

a length of flexible surgical tubing surrounding said clasp structure covering external peripheral surfaces of a portion of each clip arm extending from contiguous to said curvilinear-configuration contact means longitudinally beyond said mechanically interconnecting means to include said handle end of each clip arm and external surfaces of said chuck assembly and thumb nut means.

8. The structure of claim 1 in which said means for pivotally interconnecting said clip arms comprises:

elongated cylindrical configuration rivet means.

9. The structure of claim 8 in which said spring means comprises:

torsion spring means mounted on said revit means with a torsion arm extending toward and contacting the interior surface contiguous to the handle end of each clip arm.

10. The structure of claim 8 in which said clip arms have a U-shaped cross-sectional configuration in a plane perpendicularly transverse to the longitudinal axis of each said clip arm, with leg means of said U-shaped configuration comprising a leg on each lateral side of said clip arms, each said lateral leg presenting aperture means for receiving said rivet means.

* * * * *